United States Patent [19]

Voges

[11] Patent Number: 5,894,841

[45] Date of Patent: *Apr. 20, 1999

[54] DISPENSER

[75] Inventor: Robert Martin Voges, Sanctuary Cove, Australia

[73] Assignee: Ponwell Enterprises Limited, Wanchai, The Hong Kong Special Administrative Region of the People's Republic of China

[*] Notice: This patent issued on a continued prosecution application filed under 37 CFR 1.53(d), and is subject to the twenty year patent term provisions of 35 U.S.C. 154(a)(2).

[21] Appl. No.: 08/578,707

[22] PCT Filed: Jun. 28, 1994

[86] PCT No.: PCT/AU94/00355

§ 371 Date: Dec. 28, 1995

§ 102(e) Date: Dec. 28, 1995

[87] PCT Pub. No.: WO95/11137

PCT Pub. Date: Jan. 12, 1995

[30] Foreign Application Priority Data

| Jun. 29, 1993 | [AU] | Australia | PL9673 |
| Jul. 2, 1993 | [AU] | Australia | PL9769 |
| Aug. 31, 1993 | [AU] | Australia | PM0925 |
| Oct. 8, 1993 | [AU] | Australia | PM1709 |

[51] Int. Cl.⁶ ............................................. A61M 11/00
[52] U.S. Cl. .................. 128/203.12; 128/200.14; 128/200.16; 128/203.21; 239/102.2
[58] Field of Search ............... 128/203.12, 200.14, 128/200.16, 200.18, 200.21, 200.23, 200.22, 203.21, 203.26; 239/102.2, 4, 406

[56] References Cited

U.S. PATENT DOCUMENTS

| 4,934,358 | 6/1990 | Nilsson et al. ................ 128/200.23 |
| 4,966,579 | 10/1990 | Polaschegg ........................ 604/65 |
| 4,987,861 | 1/1991 | Lemire et al. ..................... 119/159 |
| 5,156,776 | 10/1992 | Loedding et al. ............... 128/203.12 |
| 5,284,133 | 2/1994 | Burns et al. ................... 128/200.23 |
| 5,511,726 | 4/1996 | Greenspan et al. ............... 239/102.2 |
| 5,685,485 | 11/1997 | Moele et al. ................... 239/102.2 |

FOREIGN PATENT DOCUMENTS

| 0042468 | 12/1981 | European Pat. Off. . |
| 0213753 | 3/1987 | European Pat. Off. . |
| 0234842 | 9/1987 | European Pat. Off. ........ 128/200.14 |
| 0343501 | 11/1989 | European Pat. Off. . |
| 0432992 | 6/1991 | European Pat. Off. . |
| 047557 | 11/1991 | European Pat. Off. . |
| 0542723A2 | 5/1993 | European Pat. Off. ........ 239/102.2 |
| 205820 | 1/1984 | Germany . |
| 39/08909 | 9/1990 | Germany . |
| 61-272163 | 2/1986 | Japan . |
| 2272389 | 5/1994 | United Kingdom ............ 239/102.2 |
| 87/04354 | 7/1987 | WIPO . |
| 89/06147 | 7/1989 | WIPO . |
| 92/11050 | 7/1992 | WIPO . |
| 92 15353 | 9/1992 | WIPO . |
| 93/03856 | 3/1993 | WIPO . |
| 93 11866 | 6/1993 | WIPO . |
| 93/10910 | 6/1993 | WIPO ........................ 239/102.2 |
| 93/13730 | 7/1993 | WIPO . |

*Primary Examiner*—John G. Weiss
*Assistant Examiner*—V. Srivastava
*Attorney, Agent, or Firm*—Wilson Sonsini Goodrich and Rosati

[57] ABSTRACT

A dispenser (FIG. 1, 1) comprises a reservoir (10) of a physiologically active substance and a droplet ejection device (14), for example a bubble jet or pizeoelectric device, which is controlled to issue a predetermined number of discrete droplets of the substance from ejection orifices (15) upon actuation. Device (14) may be actuated by a pressure transducer (19) responsive to inhalation and issue the droplets into an airstream (A) which enters at slot (7) and is then inhaled via mouthpiece (5). In other embodiments (FIG. 5) the dispenser is finger actuated and directed by hand for topical application. The number and/or frequency of droplets issued is programmatically controlled by a control circuit (16) whereby average and total dose of the substance are predetermined.

42 Claims, 3 Drawing Sheets

FIG.1  FIG.2

DOSE INJECTION

DISPENSER

FIELD OF THE INVENTION

This invention relates to a hand held dispensing device. The device is of particular suitability for the self-administration of physiologically active substances by inhalation and will be herein described with primary emphasis on that use but may be used for other purposes.

BACKGROUND OF THE INVENTION

There are currently three main methods for drug delivery via the respiratory tract, namely metered dose inhalers, dry powder inhalers, and nebulisers.

Metered dose inhalers ("MDI") are widely used in the management of asthma. The MDI comprises a drug packaged with a propellant in a pressurised aerosol container can having a valve which releases a volumetric metered dose of aerosol upon actuation. These devices are portable, small, and convenient to carry but deliver a dose which varies in quantity, delivery speed, and droplet size distribution as the vapour pressure of the propellant varies. The propellant pressure varies with temperature and decreases progressively as the content becomes depleted so that the range in dose variation may be substantial. Incomplete evaporation of the propellant may cause "sticking" and localised concentration of drug droplets at an impact area, and this in turn can cause undesirable side effects. For example bronchosteroids can cause local immuno-suppression and local fungal infection while local concentration of bronchodilator can lead to swallowing, with unwanted systemic affects. In addition, the use of an MDI requires a degree of synchronisation between manual valve actuation and inhalation which many users find difficult.

Dry powder inhalers ("DPI") devices rely upon a burst of inspired air to fluidise and draw a dose of an active powder into the bronchial tract. While this avoids the synchronisation problem of the MDI, DPI's are sensitive to humidity and may provoke asthma attacks in some individuals sensitive to inhaled powder. Moreover, because the force of inspiration varies from person to person, the dose administered varies.

Nebulisers generate an aerosol by atomising a liquid in a carrier gas stream and require a continuous gas compressor or bulky supply of compressed gas. In general, the droplet size of the aerosol is a function of carrier gas pressure and velocity and hence cannot be easily varied independently of concentration of the active substance in the gas stream. Inhalation reduces the pressure at the nebulizer nozzle and thus dosage and particle size are also influenced by the duration and strength of each breath. Most nebulisers operate continuously during inhalation and exhalation but special control systems can be employed to meter the aerosolised gas flow from the nebuliser to a holding chamber from which the user may draw a charge.

In general the precision of dose delivery of each of these devices is less accurate than desirable and restricts their use to drugs which have broad dosage tolerance. In each case delivery of the active agent to the intended application site is overly dependent on user technique and is variable from dose to dose and person to person. Not only is an improved delivery system required to optimise current nasal and pulmonary therapies utilising locally acting drugs but there has long been recognised a potential for the administration of many additional local and systemic drugs if a more satisfactory means of delivery were available. Medical advances suggest that pulmonary delivery of drugs such as peptides, proteins and analgesics might be of considerable advantage compared with conventional oral or injection delivery means. For example it has been suggested that insulin for diabetics may be delivered via the pulmonary route if a suitable means of delivery were available. The deposition of drug particles on lung tissue is a function of size, shape and density of particles or droplets. For many drugs, control of one or more of these factors along with precise dose or dose rate control would be desirable. However, at the present time no means of drug delivery is available which adequately meets such requirements.

Many attempts have been made to provide a cigarette substitute which provides nicotine by inhalation but which avoids the need for combustion of tobacco. Provision of a cigarette substitute involves complexities additional to those involved in the administration of a therapeutic agent. Although it is relatively easy to administer nicotine (for example in tablet form, via transdermal patches and the like), such forms do not satisfy habitual smokers because they do not satisfy important complex physiological and psychological affinities acquired by habitual smokers of combustible cigarettes.

In an attempt to provide an acceptable alternative, many cigarette substitutes have been proposed which provide nicotine on inhalation without combustion of tobacco. Conceptually, such devices are less harmful to the inhaler than smoking, avoid the hazards of passive smoking among bystanders and avoid the fire hazard and environmental problems associated with cigarette smoking. However, despite these major advantages, no device so far proposed has met with consumer acceptance.

Early cigarette substitutes employed a porous carrier impregnated with a liquid nicotine containing composition through which an air stream could be drawn to volatilize nicotine. This approach yielded insufficient nicotine per puff, suffered from a tendency for the carrier to dry out and delivered a variable amount of nicotine per puff, depending on factors such as air temperature, humidity, lung capacity of the user and amount of liquid composition remaining in the carrier.

Subsequent devices delivered nicotine from a pressurised aerosol container from which nicotine can be released by mechanical valve actuator. In one such device the valve is microprocessor controlled to limit the frequency and duration of actuation. However, the dose delivered varies with the vapour pressure of aerosol remaining in the container as well as with duration of valve actuation. The disposable pressure container, aerosol valve, and CFC propellant add considerably to active substance cost. These devices share the disadvantages of MDI devices previously discussed.

In yet other devices a nicotine containing substance is heated to vapourise an amount of nicotine which is then available for inhalation. The amount of nicotine delivered by such devices is difficult to control and is temperature dependant. In one such device a plurality of nicotine-containing pellets may be heated sequentially so that each liberates a predetermined dose. However, in that case, the dose is fixed during pellet manufacture, particle size of the aerosol is uncontrolled, and temperature of the inhaled air cannot be varied independently of dose.

Factors such as the quantity of nicotine per puff, the temperature of the puff, the draw, the presence and size distribution of flavour particles in the puff and like factors are of considerable importance in satisfying habitual smokers. The various alternatives proposed to date have simply proved unacceptable to most smokers.

To date no device has provided a satisfactory means of adjusting both the quantity of nicotine delivered in each puff in response to user demand and/or maintaining adequate precision and accuracy in the dose quantum metered out. Further the devices have failed adequately to mimic the sensations obtained during smoking.

Because the requirements for a cigarette substitute are particularly difficult to satisfy, the present invention is herein described primarily with reference to nicotine delivery, but it will be understood that the invention is more generally applicable and addresses the general need for a device which can precisely dispense doses and preferably which can dispense doses of a variety of drugs or other substances and which are adjustable from one individual to another or at different times.

Preferred embodiments of devices of the kind under consideration may be used as a less harmful form of administration of nicotine than smoking or may be used to reduce or eliminate nicotine dependence among those wishing to give up smoking.

It is, without limitation, an object of the present invention to provide a method and means for administration or self-administration of an active substance which avoids at least some of the above discussed disadvantages of prior art. It is an object of preferred embodiments of the invention to provide a method and means for dispensing the active substance for administration via inhalation.

It is an object of other preferred embodiments of the invention to provide a cigarette substitute.

DISCLOSURE OF THE INVENTION

According to one aspect the invention consists in a method for administering a substance to a human or animal subject by inhalation, said method comprising the steps of:

(i) ejecting a predetermined number of discrete droplets of the substance from at least one droplet ejection device in response to an actuation signal, and (ii) entraining the droplets in an inhalation airstream.

According to a second aspect the invention consists in a method for topical application of a substance to a human or animal subject comprising the steps of:

(1) ejecting a predetermined number of discrete droplets of the substance from at least one droplet ejection device in response to an actuation signal, and (2) directing the droplets at a selected area or region of the subject.

According to a third aspect the invention consists in an apparatus for administering a substance to a human or animal subject, said apparatus comprising:

a droplet ejection device containing a substance to be administered, means responsive to an actuation signal to eject a predetermined number of discrete droplets of the substance, and means for directing the ejected droplets at, or into, the subject.

The substance to be administered may be a therapeutic or other physiologically active agent and may be a liquid, a solution or a suspension for example a colloidal solid in a liquid carrier or an emulsion.

In preferred embodiments of the invention, the droplet ejection device ("DED") device is a piezoelectric device of the kind used in ink jet printing or is a thermal "bubble jet" device of the kind used in ink jet printing.

These devices are sometimes referred to as "droplet on demand" devices. By way of example piezoelectric devices are broadly described in "Ink-Jet Printing" [M. Doring Philips Tech Rev 40, 192–198, 1982 No. 7], while thermal devices are broadly described in "Thermal Ink-Jet Print Cartridge Designers Guide" (2nd Edition Hewlett Packard), both incorporated herein by reference.

Briefly, a typical thermal device consists of a liquid-containing chamber provided with an array of twelve coaxially divided nozzles and has twelve thin film resistors, a resistor being located directly behind each nozzle. Each nozzle supplies a droplet of liquid from the chamber if and when the corresponding resistor is energized by a short electrical pulse. The resistors thus function as ejection means. Within a few microseconds liquid in contact with the resistor is vapourised and forms a bubble. The vapour bubble grows rapidly and imparts momentum to liquid above the bubble. Some of this liquid is ejected as a droplet from the adjacent nozzle at a velocity typically exceeding 10 meters/second. The ejected volume of liquid is automatically replaced in the chamber from a reservoir by capillary action or by atmospheric pressure acting on collapsible reservoir bladder, a piston or the like. Devices of this kind when used for printing eject a typical drop of about 50 micron diameter at velocities in excess of 10 meters/second and are capable of drop ejection frequencies of up to several thousand droplets per second. The piezoelectric device generates a droplet by means of a pressure wave in the fluid produced by applying a voltage pulse to a piezoelectric ceramic which in this device acts as the ejection means. As with the thermal device, the droplet is ejected through a fine aperture. The fluid is ejected in the form of a fine droplet whose velocity depends on the energy contained in the voltage pulse. In conventional ink jet applications, ejection velocities in excess of 2 meters/second with droplet diameters of around 150 microns and droplet ejection rates of in excess of 6,000 droplets per second can be achieved.

Although conventional "droplet on demand" or "droplet ejection" devices such as used in ink jet printers may be employed in embodiments of the invention, the droplet ejection devices for use in the invention preferably differ from those used for printing. With printheads the ejection orifices are typically arranged as a rectangular matrix of, for example, 2×6 or 4×6 orifices the droplets being expelled in parallel direction from various combinations of orifice to form characters on a paper moving past the printhead at a distance of from 0.7 mm to 1.0 mm from the orifice. Droplet size is chosen to provide optimum print quality and high dot resolution. For use in the present invention there may be a smaller or greater number of orifices than used for printing and there is no need for the orifices to be arranged in a rectangular matrix with parallel orifice axes. The droplet ejection orifices may, for example, be arranged in a circle and/or may be directed at a converging or diverging angle to the axis of each other. Also for use in the present invention it is often preferred to eject much smaller droplets than are useful for printing. Additionally, the droplet ejection orifices may differ in diameter one from another so that the particle size of the active agent sprayed from the device may be controlled programmatically by selecting which orifices are used for droplet ejection and particle size may be varied from one time interval to another. Because the size of droplet ejected from the device in response to a predetermined signal is predetermined for a given liquid and device, and because the number and frequency of droplets ejected can be controlled with great precision, it is possible to closely control the total volume of liquid (dose) delivered in a given time interval. For example the device might deliver 1,000 droplets of 50 micron diameter in a second. This volume can in principle be increased or decreased in increments of one droplet.

In preferred embodiments of devices according to the invention the DED is provided with orifices of an aperture size selected to eject a droplet of less than 10 microns diameter and, more preferably, of from 1 to 5 microns diameter. Droplets may be emitted from the DED from a selected orifice in succession or from a plurality of orifices simultaneously.

In preferred embodiments the droplet delivery device or devices may be manually actuated or may actuate in response to an inhalation detector signal or other signal. The apparatus is provided with control means programmed to eject a predetermined number of droplets. The number may be varied in response to stored data and/or other input signals and programme logic may control such factors as the number of droplets ejected in a predetermined time interval, frequency of droplet ejection, the total number of droplets of active substance issued within a time period, or the like. The control means may be programmed to provide many other desirable functions as hereinafter described.

The means for directing the ejected droplets at or into the subject may for example be a simple mouth piece provided with an air inlet, a nasal shroud, face mask or other spray directing means. The active agent is typically in solution and is emitted from the DED as a fine spray which may be combined with air and/or may be heated prior to inhalation.

BRIEF DESCRIPTION OF DRAWINGS

Various embodiments of the invention will now be described by way of example only and with reference to the accompanying drawings in which:

FIG. 1 is a schematic part sectional perspective view of one embodiment of a dispenser (cigarette substitute) according to the invention; and FIG. 2 is a schematic section in an axial plane of the dispenser of FIG. 1; and FIGS. 3A, 3B and 3C are graphs showing the dispensation of an active ingredient (hatched) as a function of inhalation time in use of the embodiment of FIG. 1, and FIG. 4 is a schematic perspective view of a second embodiment of the invention, and FIG. 5 is a schematic diagram of a third embodiment of the invention.

DESCRIPTION OF PREFERRED EMBODIMENTS

With reference to FIGS. 1 and 2 there is shown a first embodiment of the invention consisting of a nicotine dispenser comprising a cigarette-shaped hollow tubular body 1 comprising connected body parts 2, 3. Body part 2 has a sidewall 4, a mouthpiece 5 at or adjacent one end and a threaded other end 6. A plurality of axially extending slots 7 penetrate side wall 4. Body part 3 is screw threaded at one end for connection with threaded end 6 of body part 2. Body part 3 is closed or constricted at the end 9 remote from mouthpiece 5.

Nicotine in a suitable solvent (for example water) is provided in a container 10 which is adapted by means of a spiggot shaped outlet and coupling 11, for fluid connection to an inlet port 12 of a droplet ejection device 14. In the present example, device 14 is of the kind used in a bubble jet printer and is provided with one or more droplet ejection orifices 15. Device 14 is controlled by control means 16, for example a microelectronic circuit or microprocessor means. Device 14 and control means 16 as well as other electrically-powered parts are energised by means of a hollow cylindrical battery 17 via an on-off switch 18 extending through side wall 14 and operable by the user. When a user inhales at mouthpiece 5, a stream of air "A" is drawn into body 1 via slots 7, through body part 2, and mouthpiece 5 into the user's lungs. Slots 7 may be provided with a damper or the like (not illustrated) to control airflow or the device may be provided with a porus plug to control airflow ("draw") on inhalation at mouthpiece 5. A pressure sensor 19 detects a change in pressure in the device due to inhalation or suction at mouthpiece 5 and issues an actuation signal via cables (not illustrated) to control means 16. Control means 16 responds to the actuation signal by issuing an output signal or signals via cables (not illustrated) to device 14 according to pre-programmed parameters or algorithms as hereinafter described. The output or "dose" signal is, or includes, a set of "eject" signals for example a train of voltage pulses. Device 14 responds to the output signal or signals by issuing a plurality of droplets of nicotine solution from orifices 15 of device 14. The liquid containing nicotine issues from device 14 as a fine spray of droplets which are entrained in the inhalation airflow from slots 7 towards mouthpiece 5. The spray typically comprises fine droplets which tend to vaporise in the airflow. Optionally, heating means 20 are provided. In that case the combination of air with nicotine droplets may be brought into thermally conductive contact with heating means 20 prior to leaving mouthpiece 5. This not only produces a sensation on inhalation similar to that obtained by smoking a combustible cigarette, but also serves to enhance the vaporisation of active substance droplets in the gas stream reducing droplet size.

In the embodiment illustrated in FIGS. 1, 2 the active substance container 10 is a collapsible bladder which is housed within a protective hollow cylindrical cartridge 21 having an air vent 22. However other forms of container (for example a cylinder fitted with a piston) could be used. Cartridge 21 is optional and serves to shield bladder 10. Container 10 is disposable or replaceable and may be adapted for fluid communication with inlet 12 of device 14 by means of a threaded, bayonet, or other suitably sealing connection.

Optionally, battery 17 may be of annular form and adapted to sleeve cartridge 21 to save space. Heating means 20 may be infrared heating plates or elements, resistance elements or the like.

Control means 16 desirably comprises a programmable logic circuit for example a microprocessor together with associated Read Only Memory (ROM), Read and Write Memory (RAM), clocks, power supply and the like and is programmed to control the quantity of nicotine delivered by the DED upon inhalation, subject to predetermined criteria.

In normal operation of the device a drop of pressure at mouthpiece 5 is detected by pressure sensor 19 which issues a signal indicative of inhalation ("actuation" signal) to control means 16 (via cables not illustrated). Control means 16 responds by issuing a "dose" signal to device 14 resulting in a spray of droplets from the device.

The dose signal typically comprises a predetermined set of drop "eject" signals which causes one or more orifices 15 of device 14 to eject a predetermined number of droplets. The dose signal may, for example, be a train of pulses (each pulse being a droplet eject signal) directed serially to one resistance heater of a thermal bubble jet device, or may be a sequence of pulses directed in parallel to a number of such resistance heaters. Since the volume of a droplet issued from a selected orifice 15 is predetermined for a given liquid and orifice, and the number of droplets ejected is controlled by the dose signal, the total volume of nicotine-containing liquid ejected in response to the actuation signal is precisely determined.

Control means 16 controls the pulse spacing, pulse width, and pulse frequency of the "dose" signal as well as the number of pulses or droplet "eject" signals and therefore determines the time interval during which droplets enter the inhalation air stream i.e. the dose rate. The number of droplets issued and/or the droplet issue frequency may be altered by changing data stored in a control memory. Control means 16 may also be programmed to address specific resistance heaters so as to emit droplets from selected orifices which may differ one from another for example in respect of diameter or orientation.

Figure 3:
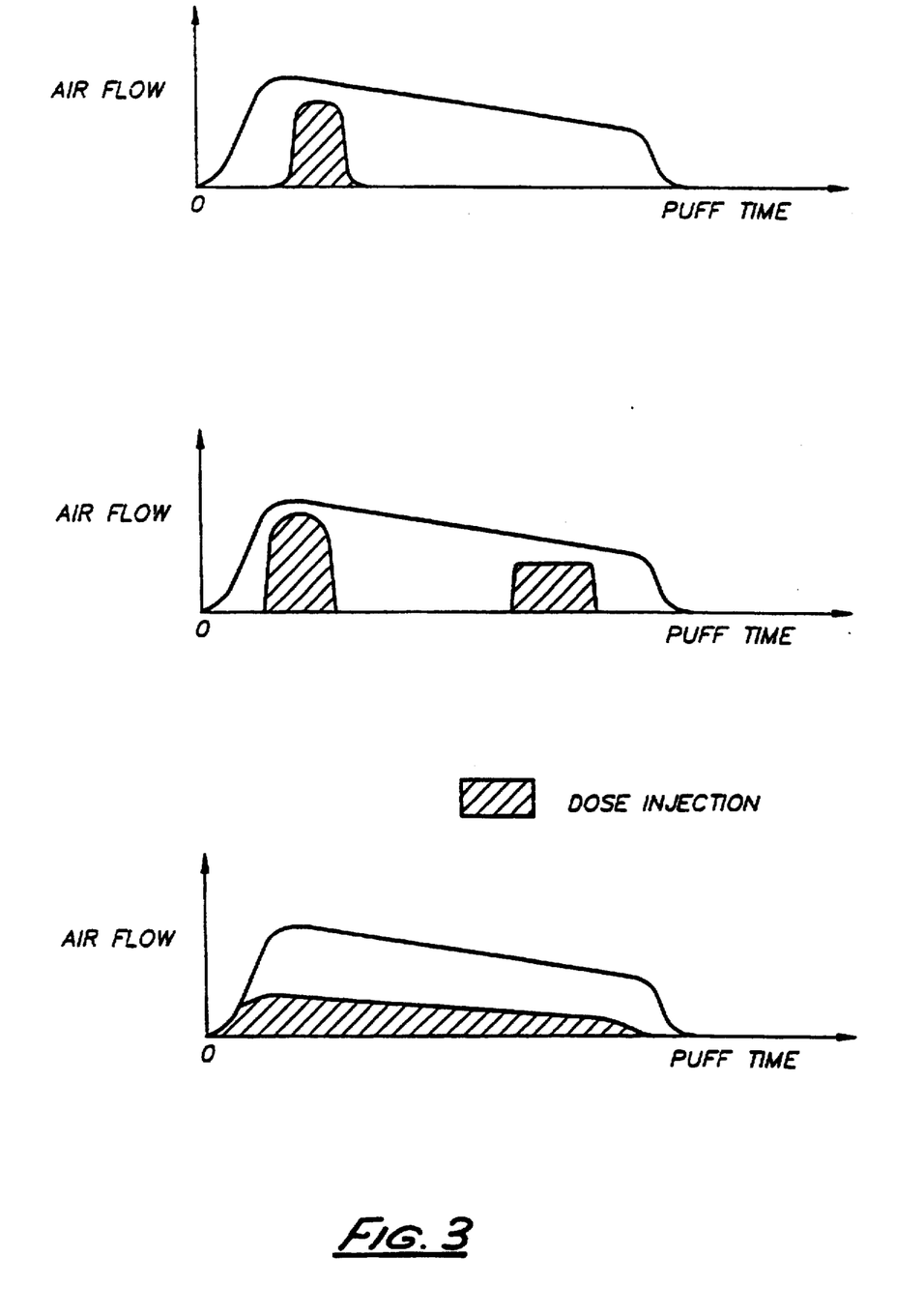

Control means 16 may also be programmed to provide a time delay between receipt of an actuation signal indicative of inhalation from pressure sensor 19 and the issuance of a "dose signal". The time delay may be varied by changing data stored in a control memory. By controlling the time delay between the leading edge of an actuation signal and issue of the dose signal, and by controlling the frequency of droplet "eject" pulses in the dose signal, the active substance can, for example, be injected into an inhaled air stream as a spike near the start (FIG. 3A) or start and end (FIG. 3B) of an inhalation "puff", or can be spread over the puff duration (FIG. 3C), or may be confined to the leading or trailing portion of a puff. This enables the change in concentration of nicotine during a puff of a cigarette to be more closely mimicked.

The control means can also be programmed to prevent a dose signal from issue until a predetermined "non repeat" time has elapsed after a preceding dose signal has been issued, notwithstanding receipt of a inhalation signal. This provides a minimum delay between successive doses.

The control means may also be provided with means for counting and storing the total number of dose signals issued within a predetermined time interval and if the total exceeds a predetermined limit (for example 30 doses in a 30 minute period) then the control circuit prevents further dose issue until a further period (e.g. 1 hour) has elapsed. This limits the maximum dose issued within an extended period.

In preferred embodiments of the invention the control means enters a minimum energy drain mode to conserve battery power if for example more than 5 minutes have elapsed since an inhalation was detected.

The apparatus of FIG. 1 may optionally be provided with means for signalling the doses remaining in the device for example by means of a plurality of LEDs 30 which progressively extinguish. Each LED may for example correspond to a dose equivalent to smoking one cigarette and the apparatus might initially store a dose corresponding to one (or several) packets of cigarettes. Other indicator means e.g. an LCD display could be used.

In summary the control means allows programmable control of factors such as:

(1) Predetermined number of droplets of nicotine issued in a single dose (dose volume).

(2) Frequency of drop issue within a dose (dose rate).

(3) Synchronization of the dose relative to commencement of inhalation.

(4) Injection of dose as a function of time from commencement of inhalation. (Pulse spacing and frequency).

(5) Control of maximum frequency of issue of successive doses or non repeat time (e.g. successive doses available at not less than 60 second intervals).

(6) Control of maximum number of doses available in a given period i.e. maximum dose rate (e.g. no more than 20 doses available per hour).

(7) Programmed variation of dose from one actuation to another (e.g. successive reduction in dose to reduce drug dependence).

(8) Programmed variation from time to time (e.g. dose to decrease from day to day).

(9) Control of nozzles from which the droplets issue (and hence spray pattern).

(10) Discrimination for adequacy of inhalation (No dose unless accompanied by sufficient inhalation air).

It will be apparent from the above that the device can be programmed in other ways and to perform other functions by the addition of other sensors—for example temperature or humidity sensors.

In addition the control means may be provided with means by which control parameters may be altered or by which the device may be reprogrammed, for example by interfacing with a keyboard or an external computer.

As will be appreciated, the microprocessor may be preprogrammed or may be user-programmable to control the operation of various DED nozzles, the heater, the airflow or the like in various other combinations, sequences, or as functions of time, temperature, or the like.

Tubular body 1 may be made of any suitable material e.g. plastics, ceramics, precious metals or the like. Mouthpiece 5 may be integral or may be soft-tip, for example of rubber or plastics cardboard, or paper and may be independently disposable. The battery may be replaceable or rechargeable. The dispenser as a whole may be provided as a disposable item or may be reusable. In the latter case, the product container and DED device will normally be replaceable or may be provided as a combined unit. In that case, the body portion will be separable e.g. via screw-threaded or bayonet coupling into sections to facilitate installation and removal of the product cartridge and/or battery. The product to be dispensed may be for example an aqueous solution of nicotine and may contain additional substances such as glycols, flavours or essences, for example menthol. The active substance may be in the form of a gel, melt, solution or suspension.

If desired, more than one DED 14 may be incorporated whereby to produce droplet streams of different droplet size and in this case, one stream may be fully vapourised by heating plates 20 while a second stream may be directed so that the user receives the sensation of a wet vapour in combination with a dry vapour as occurs when smoking conventional cigarettes.

It is not essential that the spray of active ingredient be combined with air prior to heating and if preferred the spray and/or the air may be separately heated and subsequently combined or the active ingredient may be preheated e.g. by heating means in thermal communication with storage container 10. By selective programming of the controller the smoking instrument can be adjusted to simulate "light" or "ultralight" cigarette nicotine levels or can be selectively adjustable therebetween. In other embodiments the air intake may be adjusted to vary the air to active substance ratio thus further to facilitate simulation of the sensation of smoking different kinds of cigarettes. The invention is of particular application for assisting those wishing to withdraw from cigarette smoking being programmable to progressively reduce the dose of nicotine obtainable. Devices according to the invention may either be pre-programmed, may be provided with simple means enabling the user to adjust dose within predetermined limits of safety or may be adapted to be programmed by a user e.g. by connection via an interface to a computer.

Although use of a battery is preferred other energization means for example photo cells, may be employed.

It will be understood that the apparatus described may be provided in a different form, for example with a mouthpiece which is flexible whereby the body may be held in a different orientation from the mouthpiece. Similarly the battery need not be annular and may be of any suitable shape.

Figures 1, 2:
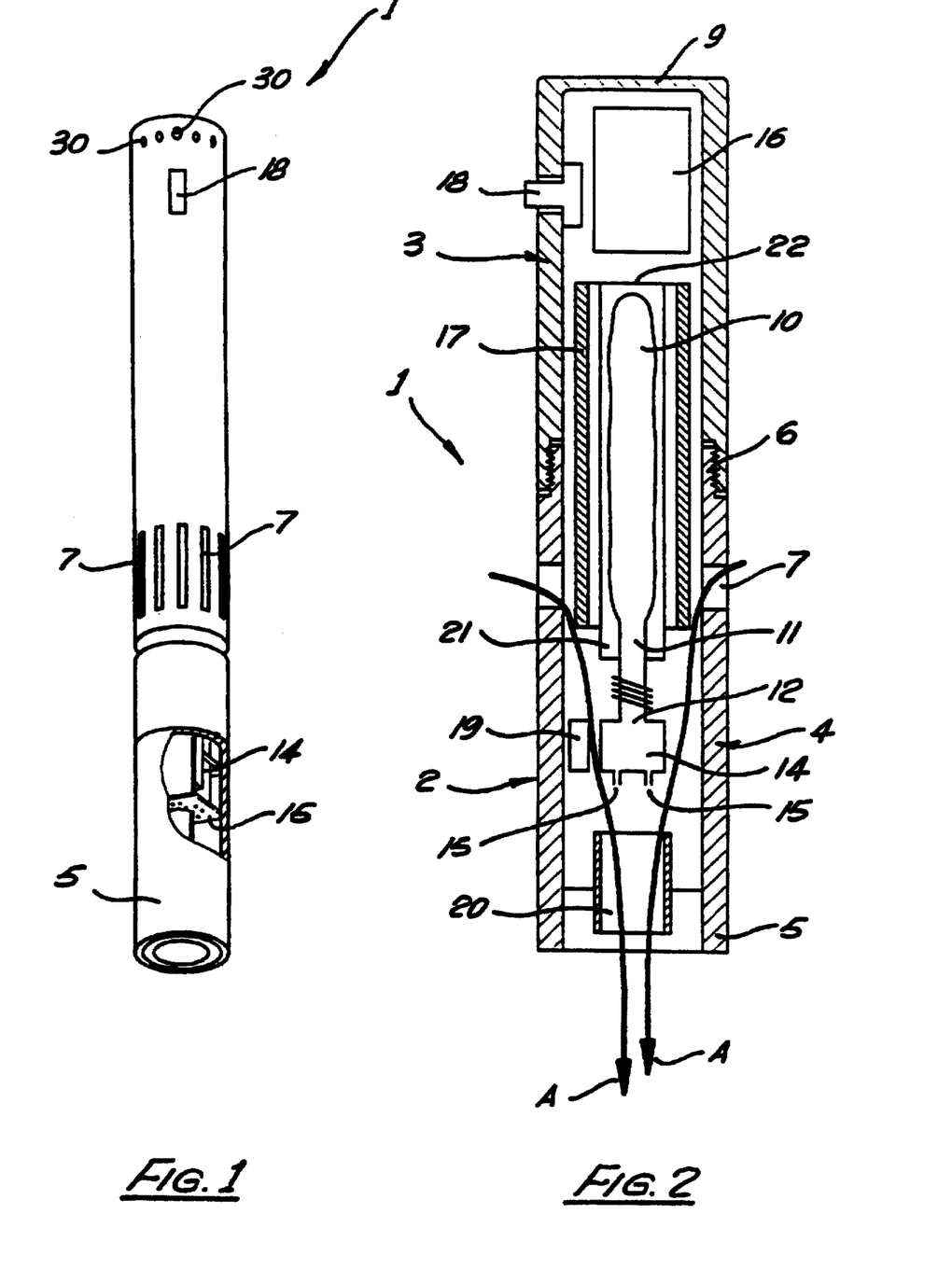
Figure 4:
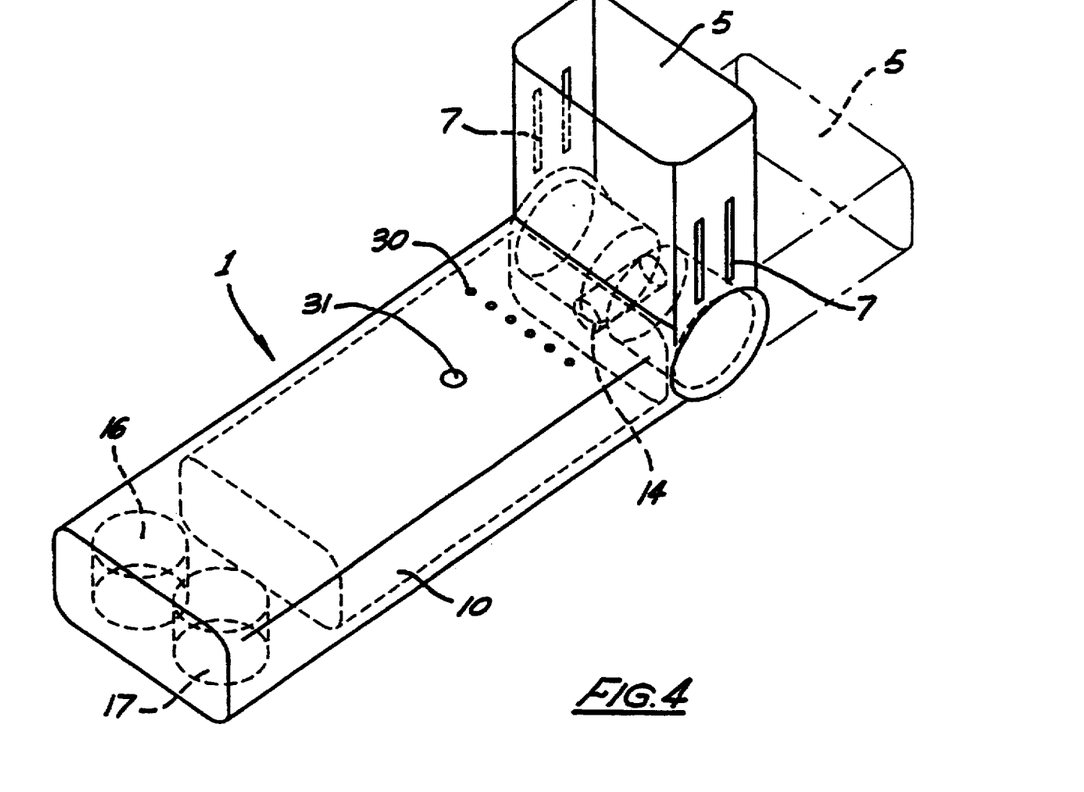

With reference to FIG. 4, there is shown another embodiment of the invention intended to dispense a bronchodilator. Parts in FIG. 4 which correspond in function to parts in FIG. 1 are identified with the same numerals. If the substance to be dispensed is heat sensitive it is preferred to use a piezoelectric DED. Disposable cartridge 10 of the embodiment of FIG. 4 contains for example, salbutamol. The embodiment of FIG. 4 differs from that of FIG. 1 in that the body is of rectangular cross-section and in that of the shape and arrangement of components differs.

A further difference is that in the embodiment of FIG. 4 the mouthpiece portion 5 is moveable hingedly between a storage position "A" in which it is in alignment with the body (shown in ghost outline in FIG. 4) and an active position "B" in which it is inclined at an angle to the body portion.

The mouthpiece may swivel about a swivel pin 40 and the swivel motion may itself actuate an on/off switch to energize the electronic control systems 16.

If desired the apparatus may be provided with manual actuation (e.g. a push-button switch, not illustrated) instead of a pressure-sensitive switch, to control the operation and initiate a "actuation" signal.

In cigarette substitute apparatus according to FIG. 1, droplet sizes of the order of 1–10 micron diameter or more are acceptable. For pulmonary administration of drugs a small droplet size is preferred. For this purpose droplet size distribution is normally described as mass median aerodynamic diameter (MMAD), with a standard deviation to indicate the degree of poly dispersity. Particles with MMAD>5 micron tend to impact on the delivery system and do not readily follow respiratory passages.

For practical purposes droplets of below 10 micron diameter and more preferably of below 5 micron diameter are therefore preferred. If necessary, droplet size can be reduced after ejection from the DED device by directing droplets at each other or at a suitable target designed to further fragment the droplets, or by injecting the droplets into an inhaled stream in a suitable manner. Optionally heating devices can be employed to vapourise the liquid and reduce droplet size.

Suitable drugs for delivery by the apparatus described include, by way of example only, analgesics, peptides and proteins. Other suitable agents include (i) $\beta_2$-bronchodilators—salbutamol, terbutaline sulphate, fenoterol hydrobromide, pirbuterol, reproterol hydrochloride, rimiterol hydrobromide, salmeterol (used extensively for treatment of acute asthma attacks and in prophylactic asthma therapy).

(ii) Antimuscarinic bronchodilators—Ipratropium bromide, oxitropium bromide (used in management of chronic bronchitis).

(iii) Corticosteroids—beclomethasone dipropionate, budesonide: used in prophylactic asthma therapy.

(iv) Sodium chromoglycate, nedocromil sodium (used in prophylactic asthma therapy) Antibiotic Therapy:

(v) Pentamidine isethionate—(antibiotic for the prophylaxis and treatment of pneumonia due to Pneumocystis carinii, a common secondary infection in HIV/AIDS patients).

Local Action (vi) Range of proprietary 'Over the Counter' nasal decongestant sprays for common cold symptoms, (vii) Corticosteroids—beclomethasone dipropionate, betamethasone sodium phosphate, budesonide, fluticasone propionate (used in prophylaxis and treatment of allergic rhinitis).

(viii) Sodium chromoglycate (used in prophylaxis of allergic rhinitis).

(ix) Anti-infective agents—e.g. dexamethasone, fusafungine, chlorhexadine hydrochloride (used in treatment of infection due to nasal staphylococci).

Systemic Action (x) Nasal administration of peptides related to antidiuretic hormone—desmopressin, lypressin (used in management of diabetes insipidus).

Apparatus for use in dispensing certain drugs may comprise programmed control means which issues a predetemined dose into each of a plurality of successive inhalations and in that case may be provided with a "dose complete" signal for example via LED 31 to indicate to a user when a full dose has been dispensed. The dose can be varied according to the composition being dispensed and the prescription for each user.

With reference to FIG. 5, there is shown a further embodiment of the invention which is adapted to dispense an active substance such as an anaesthetic, antiseptic or a liquid medication by topical application rather than by inhalation.

In surgery or medical treatment it is sometimes necessary to apply an anaesthetic, antiseptic or other fluid over a local area by means of an aerosol sprayed from a pressurised container. However it is difficult to control the amount and location of spray application. Moreover the use of CFC propellant as used in the aerosol is environmentally undesirable.

Parts of FIG. 5 corresponding in function to parts in the embodiment of FIG. 1 are identified by the same numerals.

With reference to FIG. 5 there is shown a dispenser comprising a pen shaped hollow tubular body 1 assembled from hollow body parts 2, 3. Body part 2 has a nozzle opening 25 at one end while body part 3 is closed at the dispenser end remote from nozzle opening 4. Body parts 2, 3 are separably connected at 6, for example by interengaging thread formations. A cartridge 10 is situated within body 1 and contains a liquid. Cartridge 10 is in fluid communication with one or more droplet ejector devices 14 via one or more conduits 11. In the present example DED 14 is a piezoelectric crystal or thermal resistor bubble jet device such as used in an ink jet print head. Device 14 can be energized from a battery 17 via an on off control switch 18 adapted for finger operation while the device is hand held. For example the device may be held between thumb and middle finger and may carry a push button switch 18 which is operable by the first finger. In the embodiment of FIG. 5 when control 18 is actuated, device 14 delivers liquid from cartridge 10 as a spray directed outwardly from the dispenser via nozzle 25. The duration of the spray is determined by whether the switch 8 is "on" or "off".

In a more highly preferred embodiment of the invention the volume sprayed per unit time is also be controlled. For example, the dispenser 1 is provided with one or more switches 26 (for example touch pad switches) which condition control means 16 (for example a microprocessor circuit) which in turn controls a number of bubble jet orifices 15 of device 14 through which spray droplets are emitted and/or which controls the repetition rate of device 14 and thus the number of droplets delivered in a unit of time. Thus the spray rate may be selectively light or heavy depending on the number of orifices emitting droplets and depending on the repetition rate of droplet emission.

If the device 14 is provided with a plurality of emitting orifices which are directed at preselected angles to the axis of the body, droplets of liquid may be directed in the axial direction or selectively at predetermined angles to the axial direction by circuit actuation of a selected jet orifice 15, or a selected combination of droplet ejection device jet orifices 15. In this manner a spray pattern may be selected by means of a suitable finger control forming part of a suitable micro-electric circuit controlling means 16. If all emitting orifices 15 are directed axially the spray pattern may be made selectively narrow or broad.

Alternatively control switch 26 may be adapted to select between a number of predetermined total dose dispensations or an additional control means may be provided to select total dose. In such manner, if the cartridge contains for example a liquid local anaesthetic, a surgeon can select a preset quantity and spray pattern of local anaesthetic to be applied during surgery. The surgeon could thus select between application of a small, medium or large dose, at each actuation of a switch 26 and could preselect between a narrow, medium, or broad spray pattern.

If desired the control circuit 16 may be provided with means to prevent inadvertent excessive use, for example by limiting the maximum dose of liquid which can be applied within a prespecified time period.

Also, if desired, the control circuit can be provided with security locking which overrides the on/off switch. For example the device might be provided with a programmable security code and might be incapable of issuing its contents unless and until a corresponding code is entered by an intending user.

For this purpose the device may have a plug 28, socket or transmitter/receiver which permits the device to interface with an external computer. The external computer might then also record data indicative of use, doses issued, user identification, patient identification, or similar data. The external computer may also re-enter new data in one or more memories in the control circuit of the dispenser for example dose values, time parameters, security codes. This data is then used in controlling response of the device to actuation by the user.

Other forms of hand control, for example touch sensitive switches or rotary switches may be employed instead of touch pads 26.

Control circuit 26 may utilise digital or analogue control and may employ a microprocessor, or discrete circuit components. In preferred embodiments the circuit includes a memory, preferably of type which is not erased due to lack of battery power such as a ramtron chip. The circuit further desirably includes a display screen such as a single line LCD 27. The circuit may also employ a clock and be able to utilise and display date and time data and may have a key pad or equivalent input device or may rely for input upon communication with an external key pad. The LCD could be used to display data such as number of remaining doses or time and date of last dose.

Figure 5:
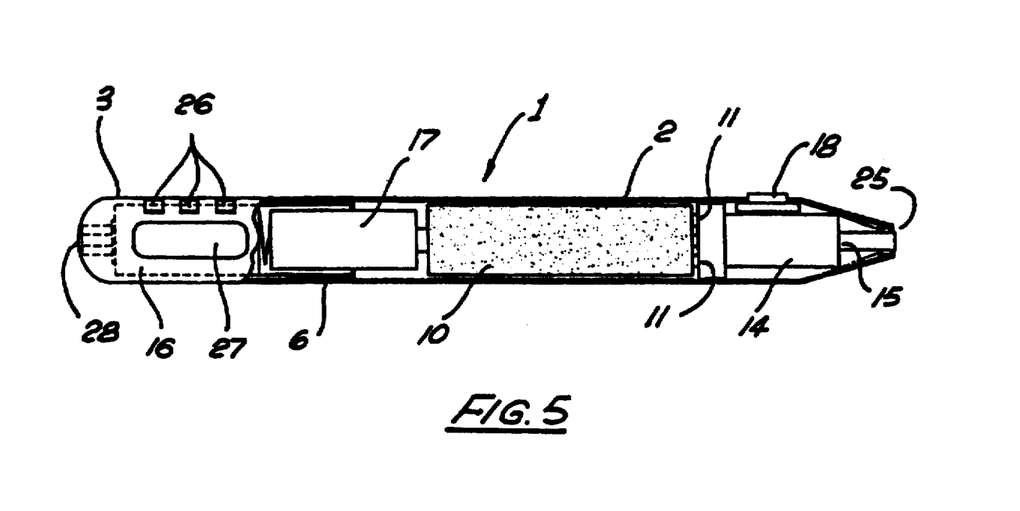

Although the embodiment of FIG. 5 has been described with reference to dispensation of a liquid it will be appreciated that the material to be dispensed can be in the form of a gel, colloid, powder suspension or any other form suitable for dispensation via the device 14.

In a further embodiment of the invention (not illustrated) the dispenser is provided with a plurality of cartridges or chambers each adapted to contain a respective medication in liquid or solution form. The control means may be programmed to provide an alarm (for example a beeper or flashing LED) at predetermined times or at predetermined times and dates. On next actuation of the device, it then delivers a predetermined dose of one medication or a combination or succession of medications each in a respective predetermined dose.

This embodiment is thus ideally suited for pre-programmed treatment of persons suffering from dementia or the like and for persons having to take a number of different medications each according to a schedule and who find self-administration confusing.

The device itself prompts the user to accept a dose and issues the appropriate doses of prescribed medication.

As will be apparent to those skilled in the art, features described in relation to one of the described embodiments may be combined with those of another.

Although the control signals have been described as pulses, those skilled in the art will appreciate that the signals can take a great variety of forms and may employ voltage or current signals, AC or DC signals, digital or analogue signals or the like, as required for operation of the DED selected. It is not necessary literally to count signals to eject a predetermined number of droplets and it will be understood that such expediencies as issuing eject signals at a predetermined frequency for a selected time interval are considered equivalent and within the scope hereof. Although the invention has been described in terms of electronic devices, fluidic devices and non electronic means of control may be employed.

Those skilled in the printing art will appreciate that with many DED devices a principal ejected droplet sometimes has trailing satellite droplets which are very much smaller. References herein to a predetermined number of droplets refer to the number of principal droplets ejected, but if necessary the DED can be calibrated to issue a desired dose taking account of satellite drops without departing from the inventive concept hereof. Likewise it will be understood that the control of liquid viscosity is important and that therefore the volume of one substance issued in response to a given set of "eject" signals will not necessarily be the same as for another substance. However those skilled in the art will have no difficulty based on the teaching hereof in programming devices according to the invention to take account of these factors.

As will be apparent to those skilled in the art from the description herein contained, the device may be embodied in other forms or arrangements and using other construction materials without departing from the scope of the invention herein disclosed.

I claim:
1. An inhaler, comprising:
   an inhaler housing;
   a mouthpiece coupled to the inhaler housing;
   a dispenser housing defining a dispensing chamber adapted to house a flowable substance to be inhaled;
   a bubble jet ejection device coupled to the dispensing chamber and including a plurality of dispensing nozzles and a plurality of heating elements, the plurality of heating elements creating bubbles of the flowable substance with sufficient momentum in the dispensing chamber to create an ejection of a portion of the flowable substance through at least one of the plurality of dispensing nozzles; and an actuation sensor coupled to the bubble jet ejection device, the actuation sensor generating an actuation signal in response to a detection of an inhalation to actuate the bubble jet ejection device.

2. The inhaler of claim 1, further comprising:

a controller coupled to the bubble jet ejection device.

3. The inhaler of claim 2, wherein the controller includes a microprocessor.

4. The inhaler of claim 2, wherein the controller includes a microelectronic circuit.

5. The inhaler of claim 2, wherein the controller includes a microprocessor coupled to a microelectronic circuit.

6. The inhaler of claim 2, wherein the controller is a programmable logic circuit.

7. The inhaler of claim 2, wherein the controller is positioned in the inhaler housing.

8. The inhaler of claim 2, wherein the controller produces a dose signal in response to the actuation signal.

9. The inhaler of claim 8, wherein the dose signal is selected from the group of a voltage, current, AC, DC, digital and analog signal.

10. The inhaler of claim 8, wherein the dispensing chamber ejects the portion of the flowable substance from at least one of the plurality of dispensing nozzles as droplets.

11. The inhaler of claim 10, wherein the controller provides an ejection of a redetermined number of droplets in a selected dose volume.

12. The inhaler of claim 10, wherein the controller provides a frequency of droplet ejection defining a dose rate.

13. The inhaler of claim 10, wherein the controller provides a synchronization of an inhalation detection and initiation of a droplet creation.

14. The inhaler of claim 10, wherein the controller provides a time spacing and frequency of droplet ejection.

15. The inhaler of claim 10, wherein the controller provides a delivery of a controlled volume of droplet ejection during a selected period of time.

16. The inhaler of claim 10, wherein the controller provides a selection of droplet delivery from at least one of the plurality of dispensing nozzles.

17. The inhaler of claim 10, wherein the controller provides a delivery of a predetermined number of droplets.

18. The inhaler of claim 10, wherein the controller provides a controlled rate of droplet delivery.

19. The inhaler of claim 10, wherein the controller counts and stores a number of dosage signals for a predetermined length of time.

20. The inhaler of claim 19, wherein the controller generates a dosage signal in response to a counting and storage of the number of dosage signals for the predetermined length of time.

21. The inhaler of claim 10, wherein the controller provides a time delay between a receipt of the actuation signal and an issuance of the dosage signal.

22. The inhaler of claim 10, wherein the controller provides a dosage complete signal.

23. The inhaler of claim 10, wherein the dosage signal is a plurality of ejection signals.

24. The inhaler of claim 23, wherein the plurality of ejection signals is directed serially to a heating element of the plurality of heating elements.

25. The inhaler of claim 23, wherein the plurality of ejection signals is directed in parallel to the plurality of heating elements.

26. The inhaler of claim 23, wherein the plurality of heating elements includes a plurality of resistors.

27. The inhaler of claim 23, wherein the plurality of heating elements includes a plurality of thin film resistors.

28. The inhaler of claim 1, wherein each of a dispensing nozzle of the plurality of dispensing nozzles is coupled to a heating element of the plurality of heating elements.

29. The inhaler of claim 28, wherein each heating element is positioned adjacent to a corresponding dispensing nozzle.

30. The inhaler of claim 10, wherein the droplets are ejected at a velocity of at least 10 meters/second.

31. The inhaler of claim 10, wherein at least a portion of the plurality of dispensing nozzles is sized to produce droplets with diameters of less then 10 microns.

32. The inhaler of claim 10, wherein at least a portion of the plurality of dispensing nozzles is sized to produce droplets with diameters of 1 to 5 microns.

33. The inhaler of claim 10, wherein the plurality of dispensing nozzles are arranged to direct the droplets at a converging angle.

34. The inhaler of claim 10, wherein the plurality of dispensing nozzles are arranged to direct the droplets at a diverging angle.

35. The inhaler of claim 10, wherein at least a portion of the plurality of dispensing nozzles have different cross-sectional diameters.

36. The inhaler of claim 10, further comprising:

a battery power source coupled to the bubble jet ejection device.

37. The inhaler of claim 36, wherein at least a portion of the battery power source is positioned in the inhaler housing.

38. The inhaler of claim 1, further comprising:

a reservoir chamber coupled to the dispensing chamber.

39. The inhaler of claim 1, wherein the flowable substance is selected from a liquid, gel, colloid and powder suspension.

40. The inhaler of claim 1, wherein the actuation sensor is an breath inhalation sensor.

41. An inhaler, comprising:

a dispenser housing defining a dispensing chamber adapted to house a flowable substance to be inhaled;

a mouthpiece coupled to the dispenser housing;

a bubble jet ejection device coupled to the dispensing chamber and including a dispensing nozzle and a heating element, the heating element generating sufficient energy to form bubbles in the dispensing chamber and effect an ejection of a portion of the flowable substance through the dispensing nozzle; and an actuation sensor coupled to the bubble jet ejection device, the actuation sensor generating an actuation signal in response to a detection of an inhalation to actuate the bubble jet ejection device.

42. An inhaler, comprising:

a dispenser housing defining a first dispensing chamber adapted to house a first flowable substance and a second flowable substance;

a mouthpiece coupled to the dispenser housing;

a bubble jet ejection device coupled to the dispensing chamber and including a first dispensing nozzle, a second dispensing nozzle, a first heating element and a second heating element, the first heating element generating sufficient energy to form bubbles in the first dispensing chamber and effect an ejection of a portion of the first flowable substance through the first dispensing nozzle, the second heating element generating sufficient energy to form bubbles in the second dispensing chamber and effect an ejection of a portion of the second flowable substance through the second dispensing nozzle; and an actuation sensor coupled to the bubble jet ejection device, the actuation sensor generating an actuation signal in response to a detection of an inhalation to actuate the bubble jet ejection device.

* * * * *